United States Patent [19]

Schnitzer et al.

[11] Patent Number: 5,610,008
[45] Date of Patent: Mar. 11, 1997

[54] METHOD OF RECOVERING ENDOTHELIAL MEMBRANE FROM TISSUE AND APPLICATIONS THEREOF

[75] Inventors: Jan E. Schnitzer, San Diego, Calif.; Bruce S. Jacobson, Amherst, Mass.

[73] Assignee: The Regents of the University of California, Oakland, Calif.

[21] Appl. No.: 461,180

[22] Filed: Jun. 5, 1995

Related U.S. Application Data

[60] Continuation of Ser. No. 124,797, Sep. 22, 1993, abandoned, which is a division of Ser. No. 928,912, Aug. 11, 1992, Pat. No. 5,281,700.

[51] Int. Cl.$^6$ ..................................................... C12Q 1/00
[52] U.S. Cl. ................................ 435/4; 436/527; 436/813
[58] Field of Search ............................... 435/4; 423/335; 436/63, 64, 518, 524, 527, 813; 530/412, 415, 416, 427, 848

[56] References Cited

U.S. PATENT DOCUMENTS

| | | | |
|---|---|---|---|
| 2,143,475 | 3/1937 | Chase | 424/569 |
| 3,551,291 | 12/1970 | Pugatch | 195/1.7 |
| 4,343,734 | 8/1982 | Lian et al. | 260/112 |
| 4,383,985 | 5/1983 | Bartorelli et al. | 424/1 |
| 4,462,215 | 7/1984 | Kuraoka et al. | 62/78 |
| 4,599,318 | 7/1986 | Bohn et al. | 436/543 |
| 4,647,455 | 3/1987 | De Bold | 424/95 |
| 4,663,289 | 5/1987 | Veech | 435/240 |
| 4,713,055 | 12/1987 | Viggiano | 604/93 |
| 4,751,284 | 6/1988 | Forssmann | 530/329 |
| 4,793,825 | 12/1988 | Benjamin et al. | 604/891.1 |
| 4,797,277 | 1/1989 | Arfors | 424/85.8 |
| 5,039,608 | 8/1991 | Goldstein et al. | 435/7.92 |
| 5,131,907 | 7/1992 | Williams et al. | 600/36 |
| 5,281,700 | 1/1994 | Schnitzer | 530/412 |

OTHER PUBLICATIONS

Jacobson, B., Isolation and Partial Characterization of the Luminal Plasmalemma of Microvascular EndoThelium From Rat Lungs, European J of Cell Biology vol. 58 296–306 (1992).
Cohen et al., *J. Cell Biol.*, 75:110–134 (1977).
Danon et al., *J. Ultrastruct, Res.*, 38:500–510 (1972).
Gotlib et al., Biochem. Biophys. Acta, 602:207–212 (1980).
Katchalsky et al., Biochem. Biophys. Acta, 33:120–138 (1959).
Patton et al., Biochem. Biophys. Acta, 816:83–92 (1985).
Scarborough, J. Biol. Chem., 250:1106–1111 (1975).
Weiss et al., Exper. Cell Res., 70:57–64 (1972).
Alles et al., Am. J. Clin. Pathol., 89:463–471 (1988).
Auerbach, Int. J. Radiat. Biol., 60:(1/2):1–10 (1991).
Belloni et al., J. Cell. Physiol., 136:398–410 (1988).
Blood et al., Biochem. Biophys. Acta, 1032:89–118 (1990).
Dvorak et al., Cancer Cells, 3(3):77–85 (1991).
Fajardo, Am. J. Clin. Pathol., 92:241–250 (1989).
Folkman, Adv. Cancer Res., 43:175–203 (1985).
Hagemeier et al., Int. J. Cancer, 38:481–488 (1986).
Jaffe, Hum. Pathol., 18:234–239 (1987).
Kaul et al., Ann. Rheum. Diseases, 50:828–832 (1991).
Mohammad et al., "Healthy and Impaired Vascular Endothelium", in Lasslo (ed.), Blood Platelet Function and Medicinal Chemistry, ch. 4, pp. 129–173 (Elsevier Biomedical: 1984).
Netland et al., Science, 224:1113–1115 (1984).
Pauli et al., Cancer Metast. Revs., 9:175–189 (1990).
Paweletz et al., Crit. Revs. Oncol./Hematol., 9(3):197–242 (1989).
Rice et al., Science, 246:1303–1306 (1989).
Vane et al., N. Eng. J. Med., 323(1):27–36 (1990).
Chaney, et al., J. Biol. Chem., 258:10062–10072 (1983).
Wasserman, et al., Biochem. Biophys. Acta, 775:57–63 (1984).
Patton, et al., Biochem. Biophys. Acta, 816:83–92 (1985).
Mason, et al., Biochem. Biophysic. Acta, 821:264–276 (1985).
Schnitzer, et al., Eur. J. Cell Biol., 52:241–251 (1990).
Jacobson, et al., Proc. Fifth World Cong. for Microcirc., p. 43, Abstract 258 (Aug. 31, 1991).

*Primary Examiner*—Ralph Gitomer
*Attorney, Agent, or Firm*—Brown, Martin, Haller & McClain

[57] ABSTRACT

A process is disclosed which makes possible the isolation of the luminal endothelial cell membrane from associated tissue. It is particularly applicable to vasculature, but broadly is applicable to all tissue cavities which are accessible from adjacent perfusable lumens. The method involves the identification of characteristic molecules (primarily proteins and lipids) associated with the luminal surface of the any endothelial membrane in situ by utilizing a novel membrane-isolation scheme to separate the endothelium from associated tissue. The normal form of that tissue of interest and diseased and/or dysfunctional forms (such as tumors) can then be examined comparatively in order to identify proteins highly enriched and/or unique for normal and abnormal endothelia. This in turn permits the production of antibodies to the proteins of interest in order to develop probes specific for the abnormal tissue, such as vasculature of a tumor. In this method, the endothelial luminal plasmalemma of a given organ is coated with colloidal silica by perfusion, a pellicle is formed, the coated area of tissue is excised and the coated plasmalemma fragments are isolated from the cognate homogenate by centrifugation. The isolated plasmalemma attached to the pellicle can then be subjected to biochemical analysis to identify and catalogue molecules characteristic of the endothelial membrane.

48 Claims, No Drawings

METHOD OF RECOVERING ENDOTHELIAL MEMBRANE FROM TISSUE AND APPLICATIONS THEREOF

STATEMENT OF GOVERNMENT SUPPORT

The Government may have rights in this invention pursuant to Grants Nos. HL-43278 and GM-29127 awarded by the National Institutes of Health.

This is a continuation of application Ser. No. 08/124,797, filed Sep. 22, 1993 now abandoned, which is a divisional of application Ser. No. 07/928,912, filed Aug. 11, 1992 U.S. Pat. No. 5,281,700.

BACKGROUND OF THE INVENTION

1. Field the Invention

The invention herein relates to methods for the analysis of endothelial cell surface molecules, primarily proteins and lipids, and use of such analyses for the diagnosis and treatment of disease.

2. Description of the Prior Art

In recent years, research in tumor biology has focused on the genetic control of tumor cell proliferation and the abnormal regulation of growth control. Although cell growth is a central aspect of the malignant phenotype, several additional processes are necessary for the full development of this phenotype in vivo. Special interactions between the neoplastic cells and the hosting vasculature are essential for tumor growth and metastasis within the body. The vascular system comprises one of the fundamental aspects of tumor biology. Most tumors depend heavily on sufficient vascularization for nutrition, growth and metastasis. The microcirculatory blood supply to many tumors limits tumor growth, size, and metastatic potential. Without the ability to recruit new blood vessels rapidly, it is likely that most tumors would remain not only quite small with a diameter of 1–2 mm (passive diffusion-limited size) but also localized to their primary site. Therefore, information gained about the interaction of tumor cells with the vasculature may provide useful information about potential mechanisms for limiting the growth and spread of neoplasms.

Most solid tumors are highly vascularized. Even though tumor microvessels are originally derived from the normal vessels, their morphology differs significantly from that of normal tissue. Early tumor development has extensive neovascularization with an increased number of intraendothelial organslies and a lack of segmental differentiation. The tumor vasculature is composed of large diameter capillaries with few if any connecting venuoles or arterioles. Even the mature or established tumor microcirculation shows extensive distortions of its capillaries which form a chaotic network of vessels with larger than normal diameters. Other distinctions between the capillaries of normal and diseased (e.g., neoplastic) tissues include increased permeability, reduced basement membrane development with altered composition, and even altered cellular composition of the blood vessels themselves. Tumor microvessels lack perivascular cells and are composed primarily of endothelial cells. It is widely believed that vessel-associated cells such as pericytes strongly influence capillary differentiation and maturation. Endothelial cells along with other cells of the vascular wall produce a variety of extracellular matrix components and the basement membrane significantly affects the final endothelial cell phenotype both in culture and in vivo. The basement membrane of tumor microvessels is significantly altered in its organization, development and molecular composition. From the available data, it is clear that the vascular environment in neoplastic tissue alters not only normal endothelial development but also its expression and secretion of molecular components comprising the basement membrane.

The vascular endothelium is critically important for human and mammalian physiology and pathology, but at present, the information needed to understand its function at the cellular and molecular level is still limited. In aggregate, the vascular endothelium of an organism amounts to a substantial mass; for instance, in humans the vasculature occupies about 300 $m^2$ which is equivalent to an organ of about 150 g weight. However, the vasculature is finely dispersed throughout the entire body and so highly diversified from one type of vessel to another and from one microvascular bed to the next, that obtaining adequate samples for the study of different endothelia is difficult and—in the microvasculature—essentially impossible.

This situation explains the paucity of biochemical data needed to understand the functions of the endothelium in terms of molecular interactions with the constituents of the blood and surrounding tissues. It also explains why most of the currently available information has been obtained from work done on endothelial cells cultured in vitro. See, for instance, Pugatch, U.S. Pat. No. 3,551,291 (1970); Wasserman et al., *Biochem. Biophys. Acta*, 775:57–63 (1984); Patton et al., *Biochem. Biophys. Acta*, 816:83–92 (1985); and Mason et al., *Biochem. Biophys. Acta*, 821:264–276 (1985). Unfortunately, not all endothelia are amenable to growth in culture and those that can be cultured exhibit both structural and biochemical drift away from that which occurs in vivo.

Identification of a number of endothelial glyco-proteins present on the surface of vascular endothelium by radioiodinating endothelial surface proteins both in situ and in culture using microspheres coated with lactoperoxidase and glucose oxidase has been reported; Schnitzer et al., *Eur. J. Cell Biol.*, 52:241–251 (1990). Although radioiodination in situ provides useful information for identifying endothelial surface proteins, it presents little direct utility in simplifying isolation of the detected proteins from the tissue specimen. In addition, radioiodination does not radiolabel all proteins equally and therefore, may only identify a subset of the proteins present on the endothelial surface. Ideally, for the purification of endothelial surface proteins, the starting material would be the endothelial membrane itself. The direct isolation of native unmodified endothelial membrane from various organs in situ or in vivo would considerably advance our understanding of the biochemistry and function of this important mediator of blood-tissue interactions, but this has previously been technically impossible.

There has been reported a procedure in which the exposed (free) surface of cultured endothelial cells are coated with a layer of cationized silica particles followed by a polyanion cross linker; Chaney et al., *J. Biol. Chem.*, 258:10062–10072 (1983). This method modifies the density of the plasmalemma since the density of colloidal silica is 2.55 $g/cm^3$ (about twice that of tissue) and allows the isolation of the coated membrane by density gradient centrifugation from endothelial homogenates.

However, the work of Chaney et al. and successors has dealt only with separation and analysis of endothelial membrane from endothelial cells in cell cultures. There has been until now no method of separating and recovering endothelial membrane directly from tissue. It is of course well known that the endothelial membrane of any organ represents only a minuscule portion of the tissue mass of that organ. When cell membranes are excised from an organ to be analyzed through conventional techniques involving homogenization and centrifugation, the endothelial cell membranes become dispersed throughout the undifferentiated tissue homogenate and isolation of membrane for separate analysis is essentially impossible. It is therefore not surprising that many researchers have opted for in vitro models using isolated endothelial cells in culture. Although these in vitro studies have yielded some insight into possible mechanisms underlying inflammation and metastasis, it is also clear that extrapolation of results using in vitro systems to the true conditions in vivo must be made very cautiously.

Previous procedures designed to investigate the biochemistry of the luminal plasmalemma of vascular endothelial cells within an intact organ (i.e., heart) relied upon in situ radioiodination. These studies have identified a number of endothelial surface proteins shown, by further analysis, to be in their majority glycoproteins with individually distinct lectin binding profiles. Although the approach has been useful as an initial attempt to identify endothelial luminal plasmalemmal proteins, it can only detect a subset of plasmalemmal proteins because it depends primarily on the presence of accessible tyrosine residues and does not label all proteins effectively.

In the overall function of the endothelium, the luminal plasmalemma plays major roles in controlling permeability, and coagulation-anticoagulation processes, as well as interactions with migrating cells in inflammatory processes and metastasis of neoplastic cells. Moreover, the luminal plasmalemma has many constitutive activities concerned with the control of vasoactive substances and also special activities inducible by cytokines that both up-regulate cell adhesion molecules and control the plasminogen activator-inhibitor system. It also interacts specifically with plasma proteins, such as transferrin, albumin, and others to internalize and transcytose selectively these ligands. Albumin binding to the endothelial glycocalyx via glycoproteins such as gp60 appears to both mediate selective transcytosis and restrict capillary permeability for other molecules. This variety of interactions occurring at the endothelial cell surface means that an endothelial plasmalemmal fraction can be a useful starting preparation for defining the molecular mechanisms of a wide variety of important cell surface functions.

Therefore, it would be of significant value to have available a method which would allow; 1) selective isolation in situ of the luminal cell membrane of endothelium from normal and diseased tissue, such as neoplastic, atherosclerotic or ischemic tissue; 2) identification of common and unique endothelial cell membrane proteins, lipids and other characteristic molecules of normal and diseased tissue; 3) identification and isolation of specific proteins or other molecules of interest for characterization, antibody production, amino acid sequencing; and 4) the ultimate use specific antibodies so produced for immunolocalizing protein expression in normal and diseased tissue with the goal of using such method as a diagnostic tool for detecting disease and dysfunctional conditions, such as tumor growth, in humans and animals and treating such diseases and dysfunctions with such antibodies.

SUMMARY OF THE INVENTION

The procedure of this invention makes possible the isolation of the luminal endothelial plasmalemma from its associated tissue. It is exemplified herein by reference to well vascularized tissues, to which it is ideally suited, but broadly it is applicable to all tissues which are accessible from adjacent perfusable lumens. Although the most immediate application involves vascular endothelium, this technique can also be used to isolate cell membranes from any tissues wherein the cell surface can be selectively coated in vivo or in situ (e.g., intestinal epithelial cell membranes by perfusion through the intestine). The method is useful in improving both early detection and treatment of many organ disease and dysfunctional conditions, particularly cancers. More specifically, this method involves the identification of characteristic molecules (primarily proteins and lipids) associated with the luminal surface of the any endothelial membrane in situ by utilizing a novel membrane-isolation scheme to separate the endothelium from its associated tissue mass. The normal form of that tissue of interest and diseased and/or dysfunctional forms (such as tumors) can then be examined comparatively in order to identify proteins highly enriched and/or unique for normal and abnormal endothelia. This in turn permits the production of antibodies to the proteins of interest in order to develop probes specific for the abnormal tissue, such as vasculature of a tumor.

In this method, the endothelial luminal plasmalemma of a given organ is coated with colloidal silica by perfusion, a pellicle is formed, the coated area of tissue is excised and the coated plasmalemma fragments are isolated from the cognate homogenate by centrifugation. The pellicle can then be separated from the isolated plasmalemma and the latter subjected to biochemical analysis to identify and catalogue the molecules characteristic to that membrane.

This method can be used to isolate these important vesicular structures that mediate endocytosis and transcytosis for endothelium. Important structures of the endothelial cell membrane, such as plasmalemmal vesicles, can now be isolated with the method of this invention.

Therefore, in one aspect the invention herein is a process for the isolation of endothelial cell membrane molecules from associated tissue which comprises forming a coating on a luminal surface of the endothelial membrane comprising particles of an adherent first ionic material which have been perfused into a luminal cavity to which the endothelial membrane is exposed; forming the coating into a pellicle adherent to a sheet of the endothelial membrane by contacting the luminal surface of the coating of first ionic material with an oppositely charged second ionic material reactive with the first ionic material; homogenizing the tissue, pellicle and endothelial membrane sheet to separate the pellicle with the endothelial membrane sheet adhered thereto from other tissue elements; and separating and isolating the molecules from the pellicle with the endothelial membrane sheet adhered thereto.

In another aspect, the invention is a process for the identification of molecules characteristic of an endothelial membrane which comprises forming a coating on a luminal surface of the endothelial membrane comprising particles of an adherent first ionic material which have been perfused into a luminal cavity to which the endothelial membrane is exposed; forming the coating into a pellicle adherent to a sheet of the endothelial membrane by contacting the luminal surface of the coating of first ionic material with an oppositely charged second ionic material reactive with the first ionic material; homogenizing the tissue, pellicle and endothelial membrane sheet to separate the pellicle with the endothelial membrane sheet adhered thereto from other tissue elements; separating and isolating the molecules from the pellicle with the endothelial membrane sheet adhered thereto; and analyzing the molecules to identify characteristic molecules associated with the endothelial membrane.

In another aspect, the invention herein is a process for the identification of an endothelial membrane from an unknown tissue which comprises forming a coating on a luminal surface of the endothelial membrane comprising particles of an adherent first ionic material which have been perfused into a luminal cavity to which the endothelial membrane is exposed; forming the coating into a pellicle adherent to a sheet of the endothelial membrane by contacting the luminal surface of the coating of first ionic material with an oppositely charged second ionic material reactive with the first ionic material; homogenizing the tissue, pellicle and endothelial membrane sheet to separate the pellicle with the endothelial membrane sheet adhered thereto from the tissue; separating and isolating the molecules from the pellicle with the endothelial membrane sheet adhered thereto; analyzing the molecules to identify characteristic molecules associated with the endothelial membrane; and comparing the identification of the characteristic molecules of the unknown type of endothelial membrane with the identifications of characteristic molecules of known types of endothelial membrane to determine the identity of the endothelial membrane.

In yet another aspect, the invention herein is a process for the diagnosis of disease or bodily dysfunction in a human or animal patient which comprises isolating a luminal system of the patient and excising at least a portion of the system containing endothelial membrane and associated tissue exposed to the luminal system from the patient; perfusing the excised portion of the system to form a coating on a luminal surface of the endothelial membrane comprising particles of an adherent first ionic material; forming the coating into a pellicle adherent to a sheet of the endothelial membrane by contacting the luminal surface of the coating of first ionic material with an oppositely charged second ionic material reactive with the first ionic material; homogenizing the tissue, pellicle and endothelial membrane sheet to separate the pellicle with the endothelial membrane sheet adhered thereto from other tissue elements; separating and isolating the molecules from the pellicle with the endothelial membrane sheet adhered thereto; analyzing the molecules to identify characteristic molecules associated with the endothelial membrane; comparing the identification of the characteristic molecules with the identification of reference characteristic molecules in a predetermined catalogue of known associations of the reference characteristic molecules with specific types of tissue, the tissue types being further identified as associated with specific conditions of disease or bodily dysfunction, and diagnosing the presence of at least one condition of specific disease or bodily dysfunction in the patient by correspondence of the characteristic molecules obtained from the patient with the disease- and bodily dysfunction-specific characteristic molecules identified in the catalogue.

In yet another aspect, the invention herein is a process for treating disease or bodily dysfunction in a human or animal patient which comprises isolating a luminal system of the patient and excising at least a portion of the luminal system from the patient, the excised portion containing diseased or dysfunctional tissue with an associated endothelial membrane exposed to the luminal system; perfusing the excised portion of the system to form a coating on a luminal surface of the endothelial membrane comprising particles of an adherent first ionic material; forming the coating into a pellicle adherent to a sheet of the endothelial membrane by contacting the luminal surface of the coating of first ionic material with an oppositely charged second ionic material reactive with the first ionic material; homogenizing the tissue, pellicle and endothelial membrane sheet to separate the pellicle with the endothelial membrane sheet adhered thereto from other tissue elements; separating and isolating the molecules from the pellicle with the endothelial membrane sheet adhered thereto; analyzing the molecules to identify characteristic molecules associated with the endothelial membrane; separating the endothelial membrane from the pellicle; analyzing the separated endothelial membrane to identify characteristic molecules associated therewith; comparing the identification of the characteristic molecules with the identification of reference characteristic molecules in a predetermined catalogue of known associations of the reference characteristic molecules with specific types of tissue, the tissue types being further identified as associated with specific conditions of disease or bodily dysfunction; diagnosing the presence of at least one condition of the disease or bodily dysfunction in the patient by correspondence of the characteristic molecules obtained from the patient with the disease- or bodily dysfunction-specific characteristic molecules identified in the catalogue; and administering to the patient medication which contains molecules which bind preferentially to at least one type of the characteristic molecules of the patient's endothelial membrane of the tissue and which medication upon the binding delivers to the diseased or dysfunctional tissue molecules antagonistic to the disease or dysfunction, such that the disease or dysfunction is reduced or eliminated.

In yet another aspect, the invention herein is a process for forming therapeutic compositions for treating disease or bodily dysfunction in a human or animal patient which comprises isolating a luminal system of the patient and excising at least a portion of the luminal system from the patient, the excised portion containing diseased or dysfunctional tissue with an associated endothelial membrane exposed to the luminal system; perfusing the excised portion of the system to form a coating on a luminal surface of the endothelial membrane comprising particles of an adherent first ionic material; forming the coating into a pellicle adherent to a sheet of the endothelial membrane by contacting the luminal surface of the coating of first ionic material with an oppositely charged second ionic material reactive with the first ionic material; homogenizing the tissue, pellicle and endothelial membrane sheet to separate the pellicle with the endothelial membrane sheet adhered thereto from other tissue elements; separating and isolating the molecules from the pellicle with the endothelial membrane sheet adhered thereto; analyzing the molecules to identify characteristic molecules associated with the endothelial membrane; separating the endothelial membrane from the pellicle; analyzing the separated endothelial membrane to identify characteristic molecules associated therewith; comparing the identification of the characteristic molecules with the identification of reference characteristic molecules in a predetermined catalogue of known associations of the reference characteristic molecules with specific types of tissue, the tissue types being further identified as associated with specific conditions of disease or bodily dysfunction; diagnosing the presence of at least one condition of the disease or bodily dysfunction in the patient by correspondence of the characteristic molecules obtained from the patient with the disease- or bodily dysfunction-specific characteristic molecules identified in the catalogue; and forming a therapeutical composition comprising molecules which bind preferentially to at least one type of the characteristic molecules of the patient's endothelial membrane of the diseased or dysfunctional tissue and which composition upon the binding delivers to the diseased or dysfunctional tissue molecules antagonistic to the disease or dysfunction, such that the disease or dysfunction is reduced or eliminated.

In various preferred embodiments, the pellicle has a density either greater or lesser by design than the density of the tissue or is magnetic and the separation of the pellicle and adhered endothelial membrane sheet from the tissue is by centrifugation or magnetic separation, respectively.

Also in preferred embodiments, the first ionic material is colloidal silica and the second ionic material is an acrylic polymer.

The common characteristic molecules will be proteins and lipids.

The catalogue from which the identifications of characteristic molecules of the endothelial membranes are made may be compiled by repeating the steps of the method of this invention to identify the characteristic molecules of endothelial membranes from a plurality of the known tissues. Such a catalogue may be in any of a variety of forms useful of researchers, physicians, and other users, such as in printed form, in the form of a computer database, and so forth.

As noted, this invention will be exemplified in terms of vascular tissue, vascular endothelial membrane and a vascular system of a subject. The invention is not limited only to vascular systems, tissue and membranes, however (although the role of the vasculature in many diseases makes it a preferred environment for the use of the claimed method); rather the method is broadly applicable to any tissue of any organ which is adjacent to a perfusable luminal cavity and which has a cell membrane exposed to such luminal cavity. It is contemplated that the method will be useful for site-specific assessment, diagnosis and treatment of all luminal-exposed tissues, including but not limited to vascular, pulmonary, cardiac, cerebral, nephric, hepatic and endocrinous tissue, and including the vascular system, lung, heart, liver, kidney, brain and numerous other organs, and also including abnormal, tumorous tissue and tumors.

DETAILED DESCRIPTION AND PREFERRED EMBODIMENTS

The invention is best understood (especially in its exemplary vasculature embodiment) by first considering the medical and physiological context of a typical target of the method, a cancerous tumor. While the exact mechanism of the present invention is not fully known, we believe that the following may represent a useful basis for understanding of the invention. It is known that there are distinct morphological differences found in tumor microvasculature as compared to normal tissue vasculature, which can be taken as evidence that the endothelial cell membrane may be different in tumors than in normal tissues. The vascular environment in tumors can be expected to alter not only the expression of secretory products (which is well documented) but also the expression of cell membrane proteins on the endothelial surface. Tumors clearly alter endothelial protein expression as indicated by differences in the expression of secretory endothelial proteins found in normal and diseased tissues. Although cell membrane protein differences have not yet been demonstrated between normal and neoplastic tissues, differences among plasmalemmal proteins from different organs have been reported. Since some of the tissue differences in the expression of endothelial surface proteins have been ascribed to differences in the local tissue environment (and especially the basement membrane), it can be expected that the disruption of the local environment for the endothelium caused by the growing tumor will also affect endothelial cell surface protein expression. Furthermore, endothelial growth and function can be altered by tumor cells either directly through their secretion of growth factors or indirectly by activation of neighboring or circulating cells which secrete other factors that affect the endothelium. Some of these factors are similar to those secreted by macrophages or lymphocytes (i.e., cytokines) which can activate endothelial cells and do alter the expression of molecules at the luminal surface of the endothelium. It is possible that endothelial activation may play a role in metastasis because in many cases the initial site-directed colonization of secondary organs by circulating cancer cells appears to be mediated by endothelial cell adhesion molecules such as selectins and integrin-like molecules. Many of these molecules were originally discovered as mediators of specific white blood cell adhesion to endothelium and are not expressed on the endothelial surface in great numbers under normal conditions but become abundant upon cell activation.

Although differentiation of molecular expression at the cell surface is expected, very little direct evidence at the molecular level is available. Phenotypic drift of cultured cells is well established, especially for endothelial cells. The novel approach of this invention alleviates many of the past hurdles in characterizing the endothelial luminal membrane from the microvasculature of both normal and neoplastic tissues in situ.

We will exemplify the method of this invention by the procedure for isolating in high yield and at a high degree of purity the endothelial luminal plasmalemma from the microvasculature of the rat lung. The procedure relies on the modification of the density of the luminal plasmalemma obtained by coating it by perfusion in situ first, with cationized colloidal silica and then with sodium polyacrylate. These steps generate a strongly adhering coat to the luminal plasmalemma that resists tissue homogenization to yield, upon repeated centrifugation using density gradients, a nearly homogeneous fraction of coated luminal plasmalemmal fragments still carrying their associated plasmalemmal vesicles. The fraction is enriched in the luminal plasmalemmal antigen, angiotensin converting enzyme, contains gp60, an antigen expected to occur on both plasmalemmal domains and is free of the mitochondrial and endoplasmic reticulum antigens so far tested. This procedure, that can be extended to any vascular bed or other luminal cell membranes, obviates the use of cultured cells for studying the biochemistry of the endothelium, at least as far as the luminal endothelial plasmalemma is concerned.

This novel method examines membrane proteins by directly isolating luminal endothelial membranes sheets from tissue in situ, through perfusing the lung vasculature with a solution of cationic colloidal silica that adheres to the luminal surface of the endothelium. After a short wash perfusion followed by perfusion with a crosslinking solution of polyacrylic acid, a stable layer of silica coats the luminal surface of the endothelium as determined by electron microscopy of the lung tissue. The luminal surface of each blood vessel has a continuous electron dense coating of silica about 1 or 2 particles in depth. More than one silica/polyacrylate can be attached by sequential perfusion of the silica to the polyacrylate. There is no evidence of leakage of the silica through the endothelial barrier to the underlying basement membrane or epithelia. The alveoli do not contain silica particles and the epithelial cells are not coated with silica. After homogenization of this tissue followed by filtration through a fine nylon mesh, electron microscopy disclosed that the flow-through crude tissue fraction contained nuclei, intracellular organelles, membranous debris, and large sheets of colloidal silica with plasma membrane and plasmalemmal vesicles still attached to it. The material restrained by the nylon filter contained very little colloidal silica-coated membrane.

The flow-through tissue fraction was mixed with 60% sucrose and sedimented for 30 min at 30,000×g. The pellet (P1) contained predominantly colloidal silica (with membrane and vesicles still attached) along with some minor contamination of nuclei and free membrane debris. This P1 pellet was resuspended in 5-(N-2,3-dihydroxypropylacetamido-[-2,4,6-triiodo-N,N-bis[2,3-dihydroxy]isophthalamide, a density gradient material commercially available under the trade name "Nycondenz™", layered over a 62–80% gradient of Nycondenz, and then sedimented at 100,000×g for 30 min, to form a second final pellet, P2. Pellet P2 is quite clean with large sheets of silica-coated membrane and little contamination of nuclei and nonspecific, noncoated membrane. By electron microscopy and immunoblotting with endothelial markers (antibodies against endothelial surface proteins such as gp60 and angiotensin converting enzyme), it is clear that this second pellet represents a significant enrichment of luminal endothelial membranes. This pellet contains extensive silica-coated endothelial membrane sheets with a characteristic abundance of plasmalemmal vesicles and a minimum of contaminating structures. Angiotensin converting enzyme, which is expected to be present only on the luminal surface of the endothelium and another endothelial marker called gp60 are both enriched significantly in the pellet fraction. Densitometric scans of the immunoblots show up to a 20-fold enrichment for ACE and a 10-fold increase for gp60 in the pellet fraction relative to the starting lung tissue homogenate. Gp60 is expected to be on both luminal and abluminal surfaces of the endothelium because it appears to be involved in receptor-mediated transcytosis of albumin via plasmalemmal vesicles. When these fractions are checked for proteins specific for intracellular organelles (mitochondrial and E.R. antigens), no signal is detected in the silica membrane pellet but ample signal is found in the total tissue homogenate and to a lesser degree in the other fractions (first spin pellet and float layer). Therefore, it appears from these experiments that this technique provides not only ample purification of endothelial membrane but also an excellent yield of specific endothelial membrane proteins as exemplified by ACE with yields approaching 95%.

In these experiments, male albino rats (Sprague-Dawley, 240–300 g) were used. Colloidal silica clad with aluminum chlorohydroxide to make it positively charged was prepared according to the procedures of Chaney et al., supra. The silica particles had a bimodal distribution of 20 nm and 50 nm (diameter) as seen in the electron microscope. Each rat was anesthetized by injecting into the thigh muscles 0.1 ml of a 3:1 mixture of 10 mg/ml ketamine and 10 mg/ml xylazine per 100 g body weight. Following tracheostomy and thoracotomy, each animal was ventilated with approximately ¼ tidal volume. The pericardium was then removed and 0.2 ml per 100 g body weight of Dulbecco's modified Eagle medium (DMEM) containing 30 μm freshly prepared nitroprusside (as a vasodilator) and 200 units heparin (as an anticoagulant) was injected into the right ventricle. After removing the thymus to fully expose the pulmonary artery and making a small cut in the right ventricle, a catheter was fed through the right ventricle into the pulmonary artery and secured with a ligature. Perfusion of the lung was begun at 18 to 22 mm Hg and a cut was made in the left atrium to allow outflow of the perfusates. At the pressure indicated, the flow rate of all the solutions was approximately 2 to 3 ml/min. The steps for coating the lung microvasculature with colloidal silica are indicated in Table I.

TABLE I

Coating the Microvasculature with Colloidal Silica and Polyacrylate

| Minutes | Solution | Rationale |
| --- | --- | --- |
| 3–5 | DMEM/nitroprusside | Remove blood from vasodilated vascular bed. |
| 4–6 | DMEM/nitroprusside | Reduce temperature of perfused lungs to 10°–15° C. |
| 1.5 | MES buffered saline, ph = 6.0 (MBS[a]) | Lower pH of vascular bed to permit optimal coating with colloidal silica. |
| 1.5 | Colloidal silica (1.5% in MBS) | To avoid lung motion, disconnect ventilator and inflate lungs with 1 cm$^3$ of air with a syringe. |
| 1.0 | MBS | Clear vasculature of unbound colloidal silica. |
| 1.5 | Sodium polyacrylate (1% in MBS) | Cross-link and shield exposed positive charges on membrane-bound colloidal silica. |
| 3–4 | HEPES buffered sucrose with protease inhibitors[b] | Flush vasculature with homogenization medium or with fixative for electron microscopy. |

Notes:
[a]MBS contains 125 mM NaCl and 20 mM 2-(N-moropholino)ethanesulfonic acid (MES).
[b]Contains 0.25 mM sucrose, 25 mM N-(2-hydroxyethyl)piperazine-N'-2-ethanesulfonic acid (HEPES) with a pH = 7.2, and 10 μg/ml each of leupeptin, pepstain A, and trans-epoxysuccinyl-L-leucyamido(4-guanidino)butane, 1 mM o-phenanthroline and 2 mM phenylmethylsulfonyl fluoride.

Isolation of the endothelial luminal plasmalemma coated with colloidal silica from the perfused lungs was accomplished by removing and trimming of large bronchi and any regions that appeared to have been poorly perfused, as indicated by their pink to red color. The remaining tissue was weighed, minced with a razor blade in a plastic dish on an aluminum block immersed in ice, then placed in 5 volumes of N-(2-hydroxyethyl)piperazine-N'-2-ethanesulfonic acid (HEPES) buffered sucrose plus protease inhibitors as indicated in Table I. The minced lungs were homogenized in the cold room using a "C" type Teflon™ pestle-glass homogenizer, 15 to 20 up and down strokes and a high speed motor running at about 1500 rpm. After filtering through a 53 nylon monofilament net, the homogenate was diluted with an equal volume of 1.02 g/ml Nycodenz, thoroughly mixed and then layered over 0.3 to 0.5 ml of 0.7 g/ml Nycodenz containing 60 mM sucrose and 25 mM HEPES, pH 7.2, in a SW60ti clear centrifuge tube. The tube was topped off with 0.25M sucrose/25 mM HEPES buffer, pH 7.2. After centrifuging the tubes for 20 min at 60,000×g, the floating tissue debris and all solutions above a glassy pellet in the bottom of the centrifuge tubes were removed by aspiration. The glassy pellet P1 contained silica-coated plasmalemmal fragments with attached plasmalemma vesicles and any contaminating debris.

Within limits, the more vigorous the homogenization the higher the yield and the degree of purity of the coated plasmalemma recovered in the first centrifugation. However, the pellet P1 is still contaminated by nuclei, chromatin and a variety of uncoated membrane components. If the homogenization is too vigorous the number of plasmalemma vesicles remaining attached to the coated plasmalemma is decreased. To reduce contamination, increase purity and, if possible, the yield of plasmalemmal vesicles, we prefer a two-stage centrifugation procedure. The coated plasmalemmal fragments were separated from occluded or associated cellular debris by resuspending the pellets in sucrose/HEPES, then diluting the suspension with an equal volume of 1.02 g/ml Nycodenz and centrifuging it to form pellet P2 that is highly purified in coated plasmalemmal fragments with much fewer plasmalemma vesicles and a light membrane fraction from which plasmalemma vesicles can be isolated.

Each step in the procedure was monitored by electron microscopy. Lungs were fixed by perfusion for 4 min with 1.5% glutaraldehyde in 0.1M sodium cacodylate-HCl buffer, pH 7.4, supplemented with 5% sucrose, following the Na polyacrylate step of Table I. Excised specimens, trimmed to small ~1 mm$^3$ blocks, were further fixed by immersion in the same fixative for 1 hour at room temperature, then washed in the same buffer (3×15 min) and finally postfixed for 60 min on ice in 1% $OsO_4$ in acetate veronal buffer, pH 7.0.

Fixed specimens were stained in block in 0.5% uranyl acetate in acetate veronal buffer and then processed through dehydration and embedding in Epon. Thin sections were cut on a Reichert Ultramicrotome, Model E, stained with lead and uranyl acetate by standard procedures and examined and micrographed using either a Philips CM 10 or a JEOL 1200 EX electron microscope.

Pellets P1 and P2 were fixed at the bottom of centrifuge tubes with 1.5% glutaraldehyde for 60 min at room temperature, rinsed and then processed as above through $OsO_4$ post fixation, uranyl acetate staining in block, dehydration and embedding. The trimmed bottom of the plastic centrifuge tube was retained in place to orient the pellet for cutting top to bottom sections for a proper survey of the contents of each pellet. The rest of the procedure was the same as in the case of tissue specimens. The retentate was fixed as above and processed on the filer and the floated fractions were fixed by mixing with equal volumes of buffered 1.5% glutaraldehyde for 15 minutes on ice followed by pelleting the fixed particles at 40,000×g for 30 min. The ensuing pellets were processed as above.

The proteins of the different tissue fractions were solubilized with cold solubilization buffer containing 0.17 M tris-HCl (pH 6.8), 3% (w/v) sodium dodecyl sulfate, 1.2% (v/v) β-mercaptoethanol, 2M urea, and 3 mm EDTA in double distilled water. After heating in boiling water for 10 min, the lysates were processed for preparative sodium dodecyl sulfate-polyacrylamide gel electrophoresis (SDS-PAGE), and the separated proteins were electro-transferred onto nitrocellulose or Immobilon™ filters in the manner described by Schnitzer et al., *Eur. J. Cell. Biol.*, 52, 241–251 [1990(A)]. Strips of these filters were immunoblotted with various rabbit anti-sera and any bound IgG was detected using either anti-rabbit IgG conjugated to alkaline phosphatase or $^{125}$I-labeled rabbit IgG antibodies in the manner described in Schnitzer et al., *Proc. Natl. Acad. Sci. USA*, 87, 6843–6847 [1990(B)]. The signal detected for each immunoblot of each fraction was quantitated using a Bio-Rad model 620 gel scanning video densitometer.

Silica was assayed in the manner described by Chaney et al., supra. Protein was determined using a bicinchoninic acid (BCA) assay kit. Both silica and proteins were difficult to determine in the original homogenate due to the turbidity of the samples. Thus, all measurements of purification in the isolated luminal plasmalemma were related to the filtered homogenate, which means that data on enrichments in the isolated plasmalemma were underestimated. Phospholipid was extracted from silica and tissue in chloroform:methanol:HCl, 1:1:0.012 (v/v/v). The homogeneous phase was separated by adding 0.25 volumes 0.15M NaCl and the upper aqueous phase was discarded. After the lower organic phase was washed with 0.25 volumes water, it was dried under a stream of nitrogen. The lipids were combusted in 10% $Mg(NO_3)_2$ in 95% ethanol and the phosphate measured and total cholesterol determined in the manner described by Higgins in Findlay et al., *Biological Membranes: A Practical Approach*, 103–138 [1987].

Perfusion of the lungs with cationic colloidal silica and polyacrylate, with the cationic colloidal silica forming a continuous coating in the luminal plasmalemma without penetrating through the endothelium into alveolar septa and spaces, was confirmed by examining perfused lung specimens by electron microscopy. Substantially all luminal endothelial surfaces were coated with a continuous layer, one to two particles thick, of colloidal silica cross-linked with polyacrylate. Rarely were there interruptions in the coating. Uncoated luminal plasmalemma areas that may occur because of vessel collapse or occlusion were rarely seen. Silica-coated leukocytes trapped in the lumina of vessels were also a rare occurrence; hence, the amount of leukocyte plasmalemma that would co-isolate with the coated luminal plasmalemma would be insignificant. The lung morphology was well-preserved without evidence of membrane blebbing, blisters, loss of membrane or other changes, relative to the controls (except for silica coating).

Silica particles adhered very closely to the plasmalemma. Plasmalemmal vesicles present either singly or in chains were in their majority not penetrated by the colloidal particles, but occasionally silica was found in a few vesicles, some of which appeared to be coated vesicles. The vesicular introits were, however, generally occupied by particles. Some vesicular profiles had short spokes which protruded on their cytoplasmic surface and probably represent infrastructure elements previously detected by high resolution scanning electron microscopy. Silica particles penetrated the luminal introit of the intercellular junctions of the endothelium but did not progress beyond the junctions proper. Flushing the microvasculature with homogenization medium after sodium polyacrylate was remarkably effective; only occasionally silica particles singly or in small clusters were found in the vascular lumina.

This method can be used to isolate these important vesicular structures that mediate endocytosis and transcytosis for endothelium. Important structures of the endothelial cell membrane, such as plasmalemmal vesicles, can now be isolated with the method of this invention.

These results confirm that the method produces a high yield of plasmalemmal fragments (assuming that silica binding is strong enough to resist homogenization) and no contamination by other organ elements such as alveolar or bronchiolar plasmalemma or components of the alveolar septa. Further, the systematic electron microscopy survey of the tissue fractions generated by the procedure gave the following results:

a) The retentate (tissue elements retained by the nylon filter) included large vessel and bronchus fragments and many smooth muscle cells, in a large amount of collagen and elastic fibers. The amount of silica-coated vascular plasmalemma lost at this step was low and was contributed primarily by large vessel endothelia, which means that subsequent fractions are expected to be enriched in luminal plasmalemmal fragments derived from the microvasculature, especially from the endothelium of capillaries.

b) The fraction floated out of the load (homogenate diluted with 1.03 g/ml Nycodenz) was comprised mostly of uncoated membrane fragments and a full complement of subcellular components (microsomes, mitochondria, etc.). There was little to no evidence of silica in this fraction.

c) The first pellet, P1, consisted primarily of large sheets of silica coated plasmalemma, just as heavily and continuously coated as in the lung in situ. Mixed with these sheets were membranous components including bits of uncoated abluminal plasmalemma apparently derived from disrupted endothelial cells. The upper part of the pellet included many intact or damaged nuclei, disrupted chromatin, cilia and basal bodies. The sheets of silica-coated plasmalemma had associated plasmalemmal vesicles, most of them not penetrated and marked by colloidal silica particles. The vesicles were similar in size and location to plasmalemmal vesicles in situ but often appeared less regular in shape.

d) The second pellet, P2, was comprised primarily of silica coated sheets of plasmalemma. Contamination by nuclei was essentially eliminated, and contamination by non-coated membranes drastically reduced and, in many regions of the pellets, eliminated. Associated plasmalemmal vesicles appeared to be less numerous and more deformed than in P1.

In general, the losses of silica-coated plasmalemma to various tissue fractions other than P1 and P2 were remarkably limited. Moreover, the pellets contained no masses of detached silica particles, which means that the adherence of the silica-polyacrylic coat to the plasmalemma is strong enough to resist homogenization and pellet shearing with minimal losses.

This visual characterization was followed by partial biochemical characterization of the luminal plasmalemma. We found that eighty percent of the silica present in the filtered homogenate was recovered in pellet P2. This figure indicates a remarkably high yield of endothelial luminal plasmalemma, since, as established by the morphology of lung and derived fractions, silica once attached to the cell surface can be used as an experimental luminal plasmalemmal marker. The yield of protein in P2 was 1.2±0.5% (n=3) of the protein of the filtered homogenate and the ratio of silica/protein in P2 relative to filtered homogenate indicated enrichment of luminal plasmalemmal proteins in P2 by a factor of 17.5. The phospholipid and cholesterol content of the membranes in P2 was comparable to that of the plasmalemma of most other mammalian cells; see Table II.

TABLE II

Partial Chemical Characterization
of Luminal Plasmalemma Isolated
from the Rat Lung Vasculature

| Component | Quantity |
| --- | --- |
| Cholesterol | 1.04 ± 0.21 µM/mg protein |
| Phospholipid | 0.93 ± 0.02 µM/mg protein |

Note: The values represent an average of three determinations.

The standard procedure used to solubilize plasmalemmal proteins was very effective in extracting the membrane proteins from the silica-membrane pellicle. When one compares the filtered homogenate, the P2 pellet, and the membranes floated out of pellet P1 in the preparation of pellet P2, P2 is enriched in three major proteins of apparent mass 80, 48 and 25 kDa. The floated fraction is in turn enriched in three other proteins of apparent molecular mass 66, 45 and 30 kDa. Comparison with previous data on myocardium endothelial proteins radioiodinated in situ [Schnitzer et al., 1990(A), supra.] suggests that the 80 and 40 kDa proteins of P2 correspond to the glycoproteins gp85/75 and gp47 which were the major radiolabeled proteins reported there. The 25 kDa protein in P2 was not radiolabeled presumably because of its inaccessibility to radioiodination reagents. (For instance, it may be located on the cytosolic aspect of the cell membrane.)

As shown by the data in Table III, the luminal plasmalemmal fraction in P2 is enriched in the following integral membrane protein antigens: gp60 (an albumin binding protein) angiotensin converting enzyme and the α subunit of the $Na^+$, $K^+$-ATPase. P2 also contains fodrin, which is a major cytoskeletal protein that lines the cytosolic aspect of the cell membrane.

TABLE III

Ratio of Antigen Concentrations in the
Plasmalemma Fraction versus the Filtered Homogenate[a]

| Antigen | Relative Amount[b] |
| --- | --- |
| Angiotensin converting enzyme | 10 |
| Albumin receptor (gp60) | 8 |
| Na, K-ATPase (α-subunit) | 5 |
| Alkaline phosphatase | >1 |
| Fodrin | 10 |
| Cytochrome oxidase (subunit 2) | Not found |
| Ribophorin II | Not found |

Notes:
[a]Proteins were isolated from the homogenate and P2 fractions, resolved by SDS-PAGE, immunoblotted with appropriate antibody and $^{125}$I-labeled second antibody; the autoradiographs were quantified by video densitometer. Both the P2 and filtered homogenate densitometer values for the antigens were normalized to unit protein before determining the P2/homogenate ratios.
[b]The values represent an average of three determinations.

These positive identification criteria are complemented by the following negative criteria. P2 tested negative for subunit 2 of cytochrome oxidase (a mitochondrial marker), and for ribophorin II (a rough endoplasmic reticulum marker). Since endothelial proteins of appropriate apparent molecular weight were detected by immunoblotting, both molecular recognition and general protein structure appear to be preserved which means, in turn, no detectable effect on plasmalemmal proteins by the silica coating procedure.

While we have shown SDS-PAGE gel extraction above, it will be evident that various standard protein purification procedures may be used including lectin affinity, size-exclusion, and ion exchange chromatography; differential detergent extractions; gel electrophoresis protein isolation and possibly high pressure liquid chromatography (HPLC). The particular purification scheme will depend on the specific characteristic of the protein of interest. Our laboratory has used several of these techniques to purify cultured endothelial cell surface proteins such as gp60 and gp18 (e.g., differential detergent extraction, lectin chromatography or ligand affinity chromatography). If the two-dimensional analysis identifies specific distinct protein "spots" that appear free of contamination from neighboring proteins on the gels, microsequencing techniques can be used for N-terminal and internal amino acid sequences. Such information will be very helpful in creating protein specific antibodies by using peptides synthesized according to the procured amino acid sequences. These antibodies can then be used in immunoaffinity chromatography to isolate the protein of interest.

It will be seen from the above data that a tissue fraction consisting of endothelial luminal plasmalemmal fragments can be obtained in high yield and remarkable level of homogeneity directly from the vascular bed of an organ, like the lung. The procedure has the advantage of obviating the use of cultured endothelial cells with attending difficulties in logistics and risk of phenotypic drift. Even though some of the endothelial cells remain unavailable, the preparation obtained is an important component in the general physiology of the vascular endothelium that can be used for further investigations.

The present invention overcomes the limitations of the prior art and can provide ample plasmalemmal material to isolate individual proteins in sufficient amounts for their full structural and chemical characterization, or for the generation of antibodies to be used for a variety of studies on the location and function of luminal plasmalemmal proteins. The yield and degree of purity of the coated plasmalemma depend upon the vigor with which the tissue is initially homogenized.

While our focus here is on the lung vasculature, we have successfully extended the procedure of this invention to other organs, including the heart, brain and liver. It is clear that this procedure is applicable to most if not all tissues. The method can provide information on the molecular basis of the extensive differentiations of the vasculature in different organs and can also serve as an informational starting base to investigate physiological modulations and pathological changes in endothelia.

Another advantage of the preferred targeting of vascular surface molecules, particularly proteins, is that the endothelial luminal surface is very accessible to probes that can be injected into the circulation. Researchers have been seeking to identify tumor-specific molecules which can be used to target specific antibodies to a tumor, primarily for diagnostic and follow-up procedures. These studies frequently have examined antigens that are specific for the tumor cells themselves. However, even with a good specific probe molecule, penetrating the vascular wall to get the probe to its target can be a significant problem with this type of approach and has severely limited the utility of such probes. The approach of the present invention has the advantage of focusing on endothelial luminal surface proteins as targets which will be exposed directly to agents administered into the circulation.

In addition, with antibodies specific for the tumor vasculature, therapeutic targeting of the tumor vasculature can be developed, such as tumor endothelium-targeted lysis, by causing complement activation at the endothelium surface with antibody directed probes. The blood supply can be blocked by using microspheres coated with tumor endothelium-specific antibodies. Because it is clear that the tumor vasculature and its full development are critical for tumor growth, metastasis, maintenance and probably survival, ablation of the blood supply specific-ally to the tumor may on its own cause significant tumor regression.

As noted, the vasculature plays a special important role in both tumor growth and metastasis (see background section for details). Therefore the method of this invention permits not only gaining basic research information on how tumors affect the vasculature and regulate synthesis of endothelial cell membrane proteins, but also identifying and purifying endothelial surface proteins specific for the tumor vasculature for both diagnostic and therapeutic tools. With antibodies specific for such proteins and this process, one may diagnose and localize the sites of primary and, it is anticipated, also metastatic lesions, and allow early detection of these lesions.

Information about the differences in protein surface expression for endothelium of different tissues may also provide useful insights about the molecular mechanisms involved in site-specific metastasis of certain tumors. Although this is not the primary focus of the present invention, such information may lay the groundwork for future investigations on the role of endothelial surface proteins in tumor metastasis.

The biomedical potential for this type of project is quite high. The process can used on human tissues for the development of medical diagnostic and therapeutic probes. For instance, vascular perfusion of human lung or renal tissue can occur after therapeutic surgical excision and the same isolation procedure optimized using the animal models can then be used to isolate luminal endothelial membrane from both normal and neoplastic human tissue. Moreover, it is also anticipated that some antibodies developed from animal models may recognize the vasculature of human tumors. If not, with the identification and eventual cloning and sequencing of vascular-specific tumor proteins in the animal models, molecular biological approaches can be used to screen human tumor tissues for expression of these proteins using DNA/RNA hybridization reactions. Highly specific monoclonal antibodies can then be made from cloned expression systems (i.e., fusion protein) which may prove to be excellent diagnostic probes and can be used to develop vascular-specific therapeutic agents.

There are a number of long-term applications and uses that we contemplate for this invention based on the above data and results:

1. Identification of specific cell surface proteins in the interaction of endothelium with hematogenous tumor cells that mediate tissue-specific metastasis in vivo.
2. Establishment of cDNA libraries for normal and diseased tissues which will be screened by specific antibodies and/or oligonucleotide probes (sequence deduced from partial amino acid sequence) in order to deduce the full amino acid sequence. Important structures of the endothelial cell membrane, such as plasmalemmal vesicles, can now be isolated with the method of this invention.
3. Use of antibodies first to label and then to destroy the vasculature in order to achieve tumor regression.
4. Use of this technology in order to develop antihuman tumor vascular-specific probes that may provide both a diagnostic and therapeutic weapon for the early detection and chemical ablation of tumors caused by smoking.

It will be evident that there are numerous embodiments of this invention which, while not expressly set forth above, are clearly within the scope and spirit of the invention. The above description is therefore intended to be exemplary only, and the actual scope of the invention is to be limited solely by the appended claims.

We claim:

1. A process for identification of a characteristic molecule associated with an endothelial membrane which is exposed to a luminal cavity, which process comprises:

a. forming on a luminal surface of said endothelial membrane, a coating of first ionic material comprising particles of an adherent first ionic material s having an affinity for said endothelial membrane which have been perfused into said luminal cavity;

b. forming said coating of first ionic material into a pellicle adherent to said endothelial membrane by contacting the luminal surface of said coating of first ionic material with an oppositely charged second ionic material reactive with said first ionic material;

c. homogenizing tissue associated with said membrane, said pellicle and said endothelial membrane and separating said pellicle with said endothelial membrane adhered thereto from other tissue elements;

d. separating and isolating molecules from said pellicle with said endothelial membrane adhered thereto; and e. analyzing molecules separated and isolated in step d. to identify a characteristic molecule associated with said endothelial membrane.

2. A process as in claim 1 wherein said pellicle has a density greater than the density of said tissue and said separating of said pellicle and adhered endothelial membrane from said tissue comprises centrifugation.

3. A process as in claim 1 wherein said pellicle is magnetic and said separating of said pellicle and adhered endothelial membrane from said tissue comprises magnetic separation.

4. A process as in claim 1 wherein tissue of step c. with which said endothelial membrane is associated is selected from the group consisting of normal and diseased pulmonary, cardiac, cerebral, nephric, hepatic and endocrinous tissue.

5. A process as in claim 4 wherein said diseased tissue is neoplastic tissue.

6. A process as in claim 1 wherein said first ionic material is colloidal silica.

7. A process as in claim 1 wherein said second ionic material is acrylic polymer.

8. A process as in claim 1 wherein said characteristic molecule is selected from the group consisting of proteins and lipids.

9. A process as in claim 1 wherein said pellicle is magnetic and said separating of said pellicle arid adhered endothelial membrane from said tissue comprises magnetic separation.

10. A process for identification of an unknown tissue having an endothelial membrane which is exposed to a luminal cavity, which process comprises:

a. forming a coating on a luminal surface of said endothelial membrane, said coating comprising particles of an adherent first ionic material having an affinity for said endothelial membrane which particles have been perfused into said luminal cavity;

b. forming said coating into a pellicle adherent to said endothelial membrane by contacting the luminal surface of said coating of first ionic material with an oppositely charged second ionic material reactive with said first ionic material;

c. homogenizing tissue associated with said membrane, said pellicle and said endothelial membrane and separating said pellicle with said endothelial membrane adhered thereto from other tissue elements;

d. separating said pellicle with said endothelial membrane adhered thereto;

e. isolating molecules from said pellicle;

f. analyzing molecules isolated in step e. to identify a characteristic molecule associated with said endothelial membrane; and g. comparing said characteristic molecule of said endothelial membrane identified in step f. with known reference characteristic molecules of known types of endothelial membrane and their tissue associations to determine the identity of said endothelial membrane and said unknown tissue.

11. A process as in claim 10 wherein said characteristic molecule of endothelial membrane associated with known tissue comprises a catalogue compiled by repeating steps a.-g. of claim 17 to identify said characteristic molecule of said endothelial membrane associated with a plurality of said known tissue.

12. A process as in claim 10 wherein said pellicle has a density greater than the density of said tissue and said separating of said pellicle and adhered endothelial membrane from said tissue comprises centrifugation.

13. A process as in claim 10 wherein said pellicle is magnetic and said separating of said pellicle and adhered endothelial membrane from said tissue comprises magnetic separation.

14. A process as in claim 10 wherein tissue of step c. with which said endothelial membrane is associated is selected from the group consisting of normal and diseased pulmonary, cardiac, cerebral, nephric, hepatic and endocrinous tissue.

15. A process as in claim 14 wherein said diseased tissue is neoplastic tissue.

16. A process as in claim 10 wherein said first ionic material is colloidal silica.

17. A process as in claim 10 wherein said second ionic material is acrylic polymer.

18. A process as in claim 10 wherein said characteristic molecule is selected from the group consisting of proteins and lipids.

19. A process as in claim 10 wherein a plurality of different types of characteristic molecules is present in said endothelial membrane and identity of said endothelial membrane and unknown tissue can be determined from any of said types of characteristic molecules of said plurality.

20. A process for identification of a characteristic molecule of a disease or dysfunction in a human or animal patient and associated with an endothelial membrane which is exposed to a luminal cavity, which process comprises:

a. forming on a luminal surface of said endothelial membrane, a coating of first ionic material comprising particles of an adherent first ionic material having an affinity for said endothelial membrane which have been perfused into said luminal cavity;

b. forming said coating of first ionic polymeric or colloidal material into a pellicle adherent to a sheet of said endothelial membrane by contacting the luminal surface of said coating of said first ionic material with an oppositely charged second ionic polymeric or colloidal material reactive with said first ionic material;

c. homogenizing tissue associated with said membrane, said pellicle and said endothelial membrane and separating said pellicle with said endothelial membrane adhered thereto from other tissue elements;

d. separating and isolating molecules from said pellicle with said endothelial membrane adhered thereto;

e. analyzing molecules separated and isolated in step d. to identify a characteristic molecule associated with said endothelial membrane;

f. comparing said identification of said characteristic molecule in step e. with previously identified molecules from endothelial membranes known to be associated with specific human or animal diseases or dysfunctions;

g. determining from said comparison the specific human or animal disease or dysfunction with which said identified characteristic molecule is associated; and h. diagnosing said disease or dysfunction in said patient.

21. A process as in claim 20 wherein said pellicle has a density greater than the density of said tissue and said separating of said pellicle and adhered endothelial membrane from said tissue comprises centrifugation.

22. A process as in claims 20 wherein said pellicle is magnetic and said separating of said pellicle and adhered endothelial membrane from said tissue comprises magnetic separation.

23. A process as in claim 20 wherein tissue of step d. with which said endothelial membrane is associated is selected from the group consisting of normal and diseased pulmonary, cardiac, cerebral, nephric, hepatic and endocrinous tissue.

24. A process as in claim 23 wherein said diseased tissue is neoplastic tissue.

25. A process as in claim 24 wherein said disease or bodily dysfunction comprises the presence in said patient of tumorous cells which express identifiable characteristic molecules on said endothelial membrane of said patient.

26. A process as in claim 20 wherein said first ionic material is colloidal silica.

27. A process as in claim 20 wherein said second ionic material is acrylic polymer.

28. A process as in claim 20 wherein said characteristic molecule is selected from the group consisting of proteins and lipids.

29. A process as in claim 20 wherein a plurality of different types of characteristic molecules is present in said endothelial membrane and identity of said disease or bodily dysfunction can be diagnosed from any of said types of characteristic molecules of said plurality.

30. A process for identification of a characteristic molecule of a disease or dysfunction in a human or animal patient and associated with an endothelial membrane which is exposed to a luminal cavity, which process comprises:
 a. forming on a luminal surface of said endothelial membrane, a coating of first ionic material comprising particles of an adherent first ionic material having an affinity for said endothelial membrane which have been perfused into said luminal cavity;
 b. forming said coating of first ionic polymeric or colloidal material into a pellicle adherent to a sheet of said endothelial membrane by contacting the luminal surface of said coating of said first ionic material with an oppositely charged second ionic polymeric or colloidal material reactive with said first ionic material;
 c. homogenizing tissue associated with said membrane, said pellicle and said endothelial membrane and separating said pellicle with said endothelial membrane adhered thereto from other tissue elements;
 d. separating and isolating molecules from said pellicle with said endothelial membrane sheet adhered thereto;
 e. analyzing molecules separated and isolated in step d. to identify a characteristic molecule associated with said endothelial membrane;
 f. comparing said identification of said characteristic molecule in step e. with previously identified molecules from endothelial membranes known to be associated with specific human or animal diseases or dysfunctions;
 g. determining from said comparison the specific human or a animal disease or dysfunction with which said identified characteristic molecule is associated; and
 h. administering an appropriate regimen of treatment of said disease or dysfunction in said patient.

31. A process as in claim 30 wherein said pellicle has a density greater than the density of said tissue and said separating of said pellicle and adhered endothelial membrane sheet from said tissue comprises centrifugation.

32. A process as in claim 30 wherein tissue of step d. with which said endothelial membrane is associated is selected from the group consisting of normal and diseased pulmonary, cardiac, cerebral, nephric, hepatic and endocrinous tissue.

33. A process as in claim 30 wherein said diseased tissue is neoplastic tissue.

34. A process as in claim 33 wherein said disease or bodily dysfunction comprises the presence in said patient of tumorous cells which express identifiable characteristic molecules on said endothelial membrane of said patient.

35. A process as in claim 30 wherein said first ionic material is colloidal silica.

36. A process as in claim 30 wherein said second ionic material is acrylic polymer.

37. A process as in claim 30 wherein said characteristic molecule is selected from the group consisting of proteins and lipids.

38. A process as in claim 30 wherein a plurality of different types of characteristic molecules is present in said endothelial membrane and as part of administration of said medication in step i. of claim 30 said molecules in said medication can bind preferentially to any of said types of characteristic molecules of said plurality.

39. A process for identification of a characteristic molecule of a disease or dysfunction in a human or animal patient and associated with an endothelial membrane which is exposed to a luminal cavity, which process comprises:
 a. forming on a luminal surface of said endothelial membrane, a coating of first ionic material comprising particles of an adherent first ionic material having an affinity for said endothelial membrane which have been perfused into said luminal cavity;
 b. forming said coating of first ionic polymeric or colloidal material into a pellicle adherent to a sheet of said endothelial membrane by contacting the luminal surface of said coating of said first ionic material with an oppositely charged second ionic polymeric or colloidal material reactive with said first ionic material;
 c. homogenizing tissue associated with said membrane, said pellicle and said endothelial membrane and separating said pellicle with said endothelial membrane adhered thereto from other tissue elements;
 d. separating and isolating molecules from said pellicle with said endothelial membrane sheet adhered thereto;
 e. analyzing molecules separated and isolated in step d. to identify a characteristic molecule associated with said endothelial membrane;
 f. comparing said identification of said characteristic molecule in step e. with previously identified molecules from endothelial membranes known to be associated with specific human or animal diseases or dysfunctions;
 g. determining from said comparison the specific human or animal disease or dysfunction with which said identified characteristic molecule is associated: and
 identifying or administering a composition for therapeutic treatment of said disease or dysfunction in said patient.

40. A process as in claim 39 wherein said pellicle has a density greater than the density of said tissue and said separating of said pellicle and adhered endothelial membrane from said tissue comprises centrifugation.

41. A process as in claim 39 wherein said pellicle is magnetic and said separating of said pellicle and adhered endothelial membrane from said tissue comprises magnetic separation.

42. A process as claim 39 wherein tissue of step d. with which said endothelial membrane is associated is selected from the group consisting of normal and diseased pulmonary, cardiac, cerebal, nephric, hepatic, and endocrinous tissue.

c. homogenizing tissue associated with said membrane, said pellicle and said endothelial membrane and separating said pellicle with said endothelial membrane adhered thereto from other tissue elements;

d. separating and isolating molecules from said pellicle with said endothelial membrane adhered thereto; and e. analyzing molecules separated and isolated in step d. to identify a characteristic molecule associated with said endothelial membrane.

2. A process as in claim 1 wherein said pellicle has a density greater than the density of said tissue and said separating of said pellicle and adhered endothelial membrane from said tissue comprises centrifugation.

3. A process as in claim 1 wherein said pellicle is magnetic and said separating of said pellicle and adhered endothelial membrane from said tissue comprises magnetic separation.

4. A process as in claim 1 wherein tissue of step c. with which said endothelial membrane is associated is selected from the group consisting of normal and diseased pulmonary, cardiac, cerebral, nephric, hepatic and endocrinous tissue.

5. A process as in claim 4 wherein said diseased tissue is neoplastic tissue.

6. A process as in claim 1 wherein said first ionic material is colloidal silica.

7. A process as in claim 1 wherein said second ionic material is acrylic polymer.

8. A process as in claim 1 wherein said characteristic molecule is selected from the group consisting of proteins and lipids.

9. A process as in claim 1 wherein said pellicle is magnetic and said separating of said pellicle arid adhered endothelial membrane from said tissue comprises magnetic separation.

10. A process for identification of an unknown tissue having an endothelial membrane which is exposed to a luminal cavity, which process comprises:

a. forming a coating on a luminal surface of said endothelial membrane, said coating comprising particles of an adherent first ionic material having an affinity for said endothelial membrane which particles have been perfused into said luminal cavity;

b. forming said coating into a pellicle adherent to said endothelial membrane by contacting the luminal surface of said coating of first ionic material with an oppositely charged second ionic material reactive with said first ionic material;

c. homogenizing tissue associated with said membrane, said pellicle and said endothelial membrane and separating said pellicle with said endothelial membrane adhered thereto from other tissue elements;

d. separating said pellicle with said endothelial membrane adhered thereto;

e. isolating molecules from said pellicle;

f. analyzing molecules isolated in step e. to identify a characteristic molecule associated with said endothelial membrane; and g. comparing said characteristic molecule of said endothelial membrane identified in step f. with known reference characteristic molecules of known types of endothelial membrane and their tissue associations to determine the identity of said endothelial membrane and said unknown tissue.

11. A process as in claim 10 wherein said characteristic molecule of endothelial membrane associated with known tissue comprises a catalogue compiled by repeating steps a.-g. of claim 17 to identify said characteristic molecule of said endothelial membrane associated with a plurality of said known tissue.

12. A process as in claim 10 wherein said pellicle has a density greater than the density of said tissue and said separating of said pellicle and adhered endothelial membrane from said tissue comprises centrifugation.

13. A process as in claim 10 wherein said pellicle is magnetic and said separating of said pellicle and adhered endothelial membrane from said tissue comprises magnetic separation.

14. A process as in claim 10 wherein tissue of step c. with which said endothelial membrane is associated is selected from the group consisting of normal and diseased pulmonary, cardiac, cerebral, nephric, hepatic and endocrinous tissue.

15. A process as in claim 14 wherein said diseased tissue is neoplastic tissue.

16. A process as in claim 10 wherein said first ionic material is colloidal silica.

17. A process as in claim 10 wherein said second ionic material is acrylic polymer.

18. A process as in claim 10 wherein said characteristic molecule is selected from the group consisting of proteins and lipids.

19. A process as in claim 10 wherein a plurality of different types of characteristic molecules is present in said endothelial membrane and identity of said endothelial membrane and unknown tissue can be determined from any of said types of characteristic molecules of said plurality.

20. A process for identification of a characteristic molecule of a disease or dysfunction in a human or animal patient and associated with an endothelial membrane which is exposed to a luminal cavity, which process comprises:

a. forming on a luminal surface of said endothelial membrane, a coating of first ionic material comprising particles of an adherent first ionic material having an affinity for said endothelial membrane which have been perfused into said luminal cavity;

b. forming said coating of first ionic polymeric or colloidal material into a pellicle adherent to a sheet of said endothelial membrane by contacting the luminal surface of said coating of said first ionic material with an oppositely charged second ionic polymeric or colloidal material reactive with said first ionic material;

c. homogenizing tissue associated with said membrane, said pellicle and said endothelial membrane and separating said pellicle with said endothelial membrane adhered thereto from other tissue elements;

d. separating and isolating molecules from said pellicle with said endothelial membrane adhered thereto;

e. analyzing molecules separated and isolated in step d. to identify a characteristic molecule associated with said endothelial membrane;

f. comparing said identification of said characteristic molecule in step e. with previously identified molecules from endothelial membranes known to be associated with specific human or animal diseases or dysfunctions;

g. determining from said comparison the specific human or animal disease or dysfunction with which said identified characteristic molecule is associated; and h. diagnosing said disease or dysfunction in said patient.

21. A process as in claim 20 wherein said pellicle has a density greater than the density of said tissue and said separating of said pellicle and adhered endothelial membrane from said tissue comprises centrifugation.

22. A process as in claims 20 wherein said pellicle is magnetic and said separating of said pellicle and adhered endothelial membrane from said tissue comprises magnetic separation.

23. A process as in claim 20 wherein tissue of step d. with which said endothelial membrane is associated is selected from the group consisting of normal and diseased pulmonary, cardiac, cerebral, nephric, hepatic and endocrinous tissue.

24. A process as in claim 23 wherein said diseased tissue is neoplastic tissue.

25. A process as in claim 24 wherein said disease or bodily dysfunction comprises the presence in said patient of tumorous cells which express identifiable characteristic molecules on said endothelial membrane of said patient.

26. A process as in claim 20 wherein said first ionic material is colloidal silica.

27. A process as in claim 20 wherein said second ionic material is acrylic polymer.

28. A process as in claim 20 wherein said characteristic molecule is selected from the group consisting of proteins and lipids.

29. A process as in claim 20 wherein a plurality of different types of characteristic molecules is present in said endothelial membrane and identity of said disease or bodily dysfunction can be diagnosed from any of said types of characteristic molecules of said plurality.

30. A process for identification of a characteristic molecule of a disease or dysfunction in a human or animal patient and associated with an endothelial membrane which is exposed to a luminal cavity, which process comprises:
  a. forming on a luminal surface of said endothelial membrane, a coating of first ionic material comprising particles of an adherent first ionic material having an affinity for said endothelial membrane which have been perfused into said luminal cavity;
  b. forming said coating of first ionic polymeric or colloidal material into a pellicle adherent to a sheet of said endothelial membrane by contacting the luminal surface of said coating of said first ionic material with an oppositely charged second ionic polymeric or colloidal material reactive with said first ionic material;
  c. homogenizing tissue associated with said membrane, said pellicle and said endothelial membrane and separating said pellicle with said endothelial membrane adhered thereto from other tissue elements;
  d. separating and isolating molecules from said pellicle with said endothelial membrane sheet adhered thereto;
  e. analyzing molecules separated and isolated in step d. to identify a characteristic molecule associated with said endothelial membrane;
  f. comparing said identification of said characteristic molecule in step e. with previously identified molecules from endothelial membranes known to be associated with specific human or animal diseases or dysfunctions;
  g. determining from said comparison the specific human or a animal disease or dysfunction with which said identified characteristic molecule is associated; and
  h. administering an appropriate regimen of treatment of said disease or dysfunction in said patient.

31. A process as in claim 30 wherein said pellicle has a density greater than the density of said tissue and said separating of said pellicle and adhered endothelial membrane sheet from said tissue comprises centrifugation.

32. A process as in claim 30 wherein tissue of step d. with which said endothelial membrane is associated is selected from the group consisting of normal and diseased pulmonary, cardiac, cerebral, nephric, hepatic and endocrinous tissue.

33. A process as in claim 30 wherein said diseased tissue is neoplastic tissue.

34. A process as in claim 33 wherein said disease or bodily dysfunction comprises the presence in said patient of tumorous cells which express identifiable characteristic molecules on said endothelial membrane of said patient.

35. A process as in claim 30 wherein said first ionic material is colloidal silica.

36. A process as in claim 30 wherein said second ionic material is acrylic polymer.

37. A process as in claim 30 wherein said characteristic molecule is selected from the group consisting of proteins and lipids.

38. A process as in claim 30 wherein a plurality of different types of characteristic molecules is present in said endothelial membrane and as part of administration of said medication in step i. of claim 30 said molecules in said medication can bind preferentially to any of said types of characteristic molecules of said plurality.

39. A process for identification of a characteristic molecule of a disease or dysfunction in a human or animal patient and associated with an endothelial membrane which is exposed to a luminal cavity, which process comprises:
  a. forming on a luminal surface of said endothelial membrane, a coating of first ionic material comprising particles of an adherent first ionic material having an affinity for said endothelial membrane which have been perfused into said luminal cavity;
  b. forming said coating of first ionic polymeric or colloidal material into a pellicle adherent to a sheet of said endothelial membrane by contacting the luminal surface of said coating of said first ionic material with an oppositely charged second ionic polymeric or colloidal material reactive with said first ionic material;
  c. homogenizing tissue associated with said membrane, said pellicle and said endothelial membrane and separating said pellicle with said endothelial membrane adhered thereto from other tissue elements;
  d. separating and isolating molecules from said pellicle with said endothelial membrane sheet adhered thereto;
  e. analyzing molecules separated and isolated in step d. to identify a characteristic molecule associated with said endothelial membrane;
  f. comparing said identification of said characteristic molecule in step e. with previously identified molecules from endothelial membranes known to be associated with specific human or animal diseases or dysfunctions;
  g. determining from said comparison the specific human or animal disease or dysfunction with which said identified characteristic molecule is associated: and
  identifying or administering a composition for therapeutic treatment of said disease or dysfunction in said patient.

40. A process as in claim 39 wherein said pellicle has a density greater than the density of said tissue and said separating of said pellicle and adhered endothelial membrane from said tissue comprises centrifugation.

41. A process as in claim 39 wherein said pellicle is magnetic and said separating of said pellicle and adhered endothelial membrane from said tissue comprises magnetic separation.

42. A process as claim 39 wherein tissue of step d. with which said endothelial membrane is associated is selected from the group consisting of normal and diseased pulmonary, cardiac, cerebal, nephric, hepatic, and endocrinous tissue.

43. A process as in claim 42 wherein said diseased tissue is neoplastic tissue.

44. A process as in claim 43 wherein said disease or bodily dysfunction comprises the presence in said patient of tumorous cells which express identifiable characteristic molecules on said endothelial membrane of said patient.

45. A process as in claim 39 wherein said first ionic material is colloidal silica.

46. A process as in claim 39 wherein said second ionic material is acrylic polymer.

47. A process as in claim 39 wherein said characteristic molecule is selected from the group consisting of proteins and lipids.

48. A process as in claim 39 wherein a plurality of different types of characteristic molecules is present in said endothelial membrane and said compositon for therapeutic treatment of step h. of claim 39 can bind preferentially to any of said types of characteristic molecules of said plurality.

* * * * *